United States Patent
Emerson et al.

(10) Patent No.: US 6,251,951 B1
(45) Date of Patent: *Jun. 26, 2001

(54) USE OF FLAVONOID AND AROMATIC ALDEHYDES AS PESTICIDES

(75) Inventors: Ralph W. Emerson; Bradford G. Crandall, Jr., both of Davis, CA (US)

(73) Assignee: Proguard, Inc, Suisun, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/479,623

(22) Filed: Jun. 7, 1995

Related U.S. Application Data

(63) Continuation-in-part of application No. 08/366,973, filed on Dec. 30, 1994, and a continuation-in-part of application No. 08/367,082, filed on Dec. 30, 1994.

(51) Int. Cl.[7] .................................................. A01N 35/02
(52) U.S. Cl. ......................... 514/701; 514/693; 424/405; 424/406; 424/407
(58) Field of Search ..................... 424/408, 417, 424/405–407, 409, 419–421, 195.18, 742, 770, 775; 514/701, 693

(56) References Cited

U.S. PATENT DOCUMENTS

| | | | |
|---|---|---|---|
| 2,465,854 | 3/1949 | Dorman et al. | 167/30 |
| 3,984,570 | * 10/1976 | Bent | 424/341 |
| 4,402,950 | 9/1983 | Wolf et al. | 424/195 |
| 4,477,361 | 10/1984 | Sperti et al. | 252/106 |
| 4,943,674 | 7/1990 | Houck et al. | 800/205 |
| 4,978,686 | 12/1990 | Sotome | 514/698 |
| 5,079,000 | * 1/1992 | Takahashi et al. | 424/195.1 |
| 5,129,951 | * 7/1992 | Vaughn | 71/122 |
| 5,149,715 | 9/1992 | Armstrong et al. | 514/701 |
| 5,166,317 | 11/1992 | Wallace et al. | 530/350 |
| 5,175,095 | 12/1992 | Martineau et al. | 435/69.1 |
| 5,177,011 | 1/1993 | Shewmaker et al. | 435/172.3 |
| 5,202,247 | 4/1993 | Kilburn et al. | 435/195 |
| 5,315,001 | 5/1994 | Krindl et al. | 536/23.6 |
| 5,340,731 | 8/1994 | Kilburn et al. | 435/179 |
| 5,639,794 | * 6/1997 | Emerson | 514/699 |

FOREIGN PATENT DOCUMENTS

| | | |
|---|---|---|
| 3724595 | 2/1989 | (DE). |
| 2529755 | 6/1983 | (FR). |
| 504125 | 5/1939 | (GB). |
| 57120501 | 7/1982 | (JP). |
| 86025682 | 7/1982 | (JP). |
| 60-146804 | 8/1985 | (JP). |
| 61-007290 | 1/1986 | (JP). |
| 61-065802 | 4/1986 | (JP). |
| 63-255203 | 10/1988 | (JP). |
| 1261303 | 10/1989 | (JP). |
| 2157205 | 6/1990 | (JP). |
| 4149103 | 5/1992 | (JP). |

(List continued on next page.)

OTHER PUBLICATIONS

Mahmoud—Antifungal–Essential Oils: Letters. App.Micro. 19; 110–113 1994.*

Horst et al Plant Disease vol 76 #3 1992.*

Greef et al Mitt.Biol.Bundesanst.Landrorstwirtsch #266, p. 220 1990.*

Bullerman et al.J.Food Science 42 (4) 1977 pp.1107–1109.*

Keene et al Physiol. Plant Path. vol14(3) pp. 265–280 1979.*

Hagiwara et al: Hokkaido Sochi Kenkyukaiho pp. 74–77, 27, 1993.*

Yuan et al Fundamental & Applied Toxicology 20:83–87, 1993.*

Mawo et al Outlook on Agriculture vol 7 #5 p. 231–235 1973.*

Vaughn et al: J Agric. Food Chem(1994), 42 (1),200–3 Antifungal Activity of Natural Compounds—.*

Gorris et al Brighton Crop Prot. Conf–Pests Dis. 1994;vol. 1; 307–12 : Control of Fungal Storage Cleaner of Potato—.*

Sitaramaiah et al. *Chemical Abstracts* (1982) 96(13) (Abstract No. 99381).

Lamb C. J. et al. *Bio/Technology* (1992) 10:1436–1445.

Bowles & Miller, *J. Food Protection* (1993) 56: 788–794.

Casey & Dobb, *Enzyme Microb. Technol.* (1992) 14: 739–747.

Yuan et al., *Fundamental & Applied Toxicol.* (1993) 20: 83–87.

Ishibashi & Kubo, *Proc. Assc. Plants* (1987) 33: 122–125.

King, *Agriculture Handbook* (1954) 69: 1–397 (relevant pages attached).

Matsumoto Microbiology Laboratory, *Antimicrobial Test of Avion–M* (1982) 57–07 (full cite not available).

Frear, *Chemistry of Insecticides and Fungicides* (1942 13 184–191.

Ishibashi et al, *Nematicidal effect of cinnamic aldehyde on root–knot nematode, Meloidgyne incognita* (1987) 33: 122–125.

Hagiwara et al, *Effect of cinnamaldehyde on the growth of Rhizoctonia solani (AG2–2 IIIB) and development of brown patch disease on bentgrass* (1993) 27: 74–77.

Ohtsuka et al, *Effects of Abion CA chemicals on vegetable diseases* (1983) 29: 48–51.

*Primary Examiner*—Neil S. Levy
(74) *Attorney, Agent, or Firm*—Barbara Rae Venter; Rae-VenterLaw Group, PC

(57) ABSTRACT

Methods and compositions based upon natural flavonoid and aromatic aldehydes are provided, which find use as pesticides. The compositions are effective against pathogenic fungi and insects at concentrations which are not phytotoxic to the treated host plant. Infestations of a variety of plant parts can be treated, including those of leaves and roots. Susceptible organisms include rust, powdery mildew and aphids.

16 Claims, No Drawings

FOREIGN PATENT DOCUMENTS

| | | |
|---|---|---|
| 4176460 | 6/1992 | (JP) . |
| 6183925 | 8/1992 | (JP) . |
| 4316506 | 11/1992 | (JP) . |
| 5117125 | 5/1993 | (JP) . |
| 5139924 | 6/1993 | (JP) . |
| 06329514 | 11/1994 | (JP) . |
| WO93/05159 | 3/1993 | (WO) . |
| WO93/24638 | 12/1993 | (WO) . |
| WO94/08036 | 4/1994 | (WO) . |
| WO94/24158 | 10/1994 | (WO) . |
| WO94/27434 | 12/1994 | (WO) . |
| WO95/15082 | 6/1995 | (WO) . |
| WO 96/20596 | 7/1996 | (WO) . |
| WO 96/41528 | 12/1996 | (WO) . |

* cited by examiner

USE OF FLAVONOID AND AROMATIC ALDEHYDES AS PESTICIDES

CROSS-REFERENCE TO RELATED APPLICATIONS

This application is a continuation-in-part of U.S. Ser. Nos. 08/366,973, Ser. No. 08/367,082 filed on Dec. 30, 1994, which is related to two copending applications filed on Dec. 30, 1994, namely and U.S. Ser. No. 08/366,974, which disclosures are herein incorporated by reference.

INTRODUCTION

1. Technical Field

The present invention is related to the biocontrol of plant pathogens through nutritional mediation. The invention is exemplified by the use of cinnamic aldehyde and coniferyl aldehyde to control growth of fungi and parasitic insects, including sap sucking insects which colonize the surfaces of plant parts and tissues.

2. Background

The surfaces of plant parts such as roots and leaves are colonized by a variety of organisms, many of which are dependent upon the host plant as a source of nutrients. The colonizing organisms include pathogenic fungi and sap-sucking insects; both groups are capable of inflicting severe damage to the host plant, including stunting the growth of the host plant and decreasing plant productivity, to killing the host plant.

Fungi pathogenic for plants are many and diverse. They occur in most groups of fungi. A few, such as rusts, Uredinales, and powdery mildew and downy mildew, Erysiphacea and Peronosporacea, are obligate parasites. Generally, a particular rust or mildew is associated with specific host plants which elaborate nutrients required by the pathogen. As an example, rust, caused by *Phragmidrium mucronatrum*, is an important fungal disease associated with roses; it produces bright orange pustules on the underside of rose leaves and pale yellow spots on the top. Powdery mildew, caused by *Sphaerotheca pannosa* (Wallr. ex. Fr.) Lev var. rosae Woronichine also is associated with roses and is probably the most widely distributed and serious disease of glasshouse, garden, and field-grown roses alike.

Pathogenic insects which infest plants include those insect species which are symbiotic with bacteria, such as aphids, leaf hoppers, and white fly; the host insect cannot survive without the symbionts. As an example, aphids (homoptera) possess symbiotic bacteria of the genus Buchnera in cells called mycetocytes within the hemocoel. The bacteria are transmitted directly from the maternal aphid to her offspring and aposymbiotic aphids do not occur naturally. The bacteria may provide lipids which are required for embryogenesis of the host insect but which are absent or in low concentrations in phloem sap in plants infected by the insects.

The plant pathogens include the grape phylloxera (*Daktulosphaira vitifoliae*), an aphid-like insect, and nematodes. Phylloxera is native to the United States east of the Rocky Mountains, where it lives on native wild species of grapes, which have evolved resistance to the feeding of the insect. The European grape (*Vitis vinifera*), which is used to produce wine, evolved in western Asia and has no resistance to phylloxera. Stem and bulb nematode (*Ditylenchus dipsaci*) has been recorded from all the major agricultural regions in California This wide distribution probably reflects its spread on such infested planting material as garlic cloves. Wherever such infested material is grown, the nematode may be introduced. *Ditylenchus dipsaci* can be found parasitizing a wide range of cultivated and wild plants. Nematodea produce galls in infected tissue. In addition to the disturbance caused to plants by the nematode galls themselves, damage to infected plants is increased by certain parasitic fungi, which can easily attach the weakened root tissues and the hypertrophid, undifferentiated cells of the galls. Moreover, some fungi, for example, Pythrium, Fusarium, and Rhizoctonia, grow and reproduce much faster in the galls than in other areas of the root, thus inducing an earlier breakdown of the root tissues.

A variety of pesticide compositions are used for controlling plant pathogens. For example, protective fungicidal sprays on a 6–7 day schedule for both rust and powdery mildew when environmental conditions favor disease development are the typical means of control. Two frequently used systemic fungicides are benomyl and triforine. However, the cost of fungicides for control of powdery mildew is high: in cut rose crops the cost of treatment in the State of California is several million dollars a year.

The older fungicides include inorganic compounds such as copper and sulphur and the organic protectants such as thiram, captam, maneb, and chlorotholonil. These compounds act only at the surface of the plant and must be present at or before appearance of the fungal pathogen in order to prevent infection. These older fungicides are multisite inhibitors; i.e., they affect many metabolic activities in a fungus. The newer fungicides tend to be highly effective organic systemics such as benzimididazoles, sterol biosynthesis inhibitors, carboxanilides, and phenylamides which act internally as well as at the plant surface. In contrast to the older surface protectants, the systemic fungicides are generally effective at much lower dosages and can cure established fungal infections, a critical factor in disease management. The systemic fungicides usually act at a single target site in the fungus, interfering with specific metabolic processes that are necessary for production of all new cell material required for growth, maintenance, and virulence of the fungal organism. These preparations typically are effective only against fungal pathogens.

Current methods of chemical control for certain aboveground pests (e.g., spider mite, aphids, silverleaf white fly, leaf hoppers) include those which combine two insecticides from different chemical classes, for example, combining a synthetic pyrethroid with an organophosphate or organochlorine insecticide. Soil fumigants have been a popular treatment for soil pests (nematodes, phylloxera). Use of certain highly effective types of insecticides and fumigants has sharply decreased in recent years due to cancellations of public regulatory agency registrations, or refusals of re-registrations, of products.

The wide-spread use of pesticides has resulted in the development and evolution of resistant pathogens, as well as growing environmental and health care concerns. A highly visible ecological-environmental activist community and public regulatory agencies have resulted in fewer and fewer pesticide registrations and, consequently, less related research and development.

The use of flavonoid and aromatic aldehydes for treatment of both fungal and other pathogens has been reported. However the preparations used have been reported to require the use of expensive antioxidants, and at the concentrations used, would be expected to be phytotoxic to the host plant. Such formulations also are reported to require multiple applications to ensure continued protection of the host plant. It therefore is of interest to identify and/or develop, "biorational" fungicides which have lower animal and environmental toxicities and which also do not exhibit significant phytotoxicity at the concentrations used to control pathogenic fungi and insects.

3. Relevant literature

A method of protecting crops from attack of insect pests, microorganisms and pathogenic microbes using a composition comprising cinnamic aldehyde and requiring an antioxidant is disclosed in U.S. Pat. No. 4,978,686. Protection of crops against pathogenic microorganisms and insect pests by applying an aqueous composition containing a cinnamaldehyde is disclosed in French patent application 2529755. U.S. Pat. No. 2,465,854 describes an insecticidal composition containing a cinnamic aldehyde derivative. Control of Verticillium using cinnamaldehyde in the substrate in which mushrooms are grown is disclosed in U.S. Pat. No. 5,149,715.

Reweri, et al. describe induction of systemic resistance to powdery mildew in cucumber by phosphates. *Biol. Agic. and Hort.* (1993) 9:305–315. Horst and Kawamato disclose the effect of sodium bicarbonate and oils on the control of powdery mildew and black spot on roses. *Plant Disease*, March 1992, p.247. Sodium bicarbonate and severely solvent refined light paraffinic petroleum oil have been used to control black spot and powdery mildew. Ziv et al., *Hort. Science* (1993) 28:124–126.

Elad et al. disclose the effect of film-forming polymers on powdery mildew of cucumber. *Phytoparasitica* (1989), 17:279–288. Hagiladi and Ziv disclose the use of antitranspirant for the control of powdery mildew in the field. *J. Environ. Hortic.* (1986), 4:69–71. Macro, et al. disclose control of powdery mildew of roses with antitranspirant coating polymers. *Phytoparasitica* (1994) 22:19–29. Paulus and Nelson disclose use of flusilarzol, myciobutanil, fenarimol, pentonazote, and diniconazole for controlling powdery mildew and rust in roses. *Calif. Agric.* 1988, 42:15.

U.S. Pat. No. 4,402,950 describes the deactivation of viruses inside lining human and animal organisms by application of a terpene obtainable from aromatic plants by steam application. The terpenes cited are: black pepper oil, cinnamon flour oil, cardamon oil, linallyl acetate, cinnamic aldehyde, safrol, carvon and cis/trans citrao. U.S. Pat. No. 4,477,361 describes a cinnamic compound containing an anti-microbial surfactant which is rendered substantive to the surface being washed.

References relating to anti-microbial properties of various saponins either alone or in combination with other agents include the following: JP2157205, DE3724595, JP61065802, JP61007290.

SUMMARY OF THE INVENTION

The present invention provides a method for controlling pathogenic organisms on plants, as well as seeds, seedlings and plants substantially free of plant pathogens through nutritional mediation. The method includes the step of contacting one or more parts or tissues of a diseased plant or a plant susceptible to attack by pathogens with an antipathogenic agent in an amount sufficient to control growth of target pathogenic organisms. The growth modulating product has a formula shown in (1) below:

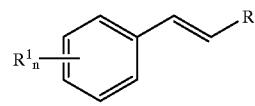

(I)

wherein R represents —CH$_2$OH or —CHO; n is an interger from 0 to 3; and each R$^1$ independently represents OH or an organic substitutent containing from 1 to 10 carbon atoms and from 0 to 5 heteroatoms, wherein the total number of carbon and heteroatoms in all R$^1$ substitutents of said compound is no more than 15. These compounds include natural compounds such as cinnamaldehyde, coniferyl aldehyde, and closely related compounds. The method finds use in treating ornamentals and agricultural crops for pathogenic organisms.

DESCRIPTION OF SPECIFIC EMBODIMENT

Seeds, seedlings, plants, and plant parts such as fruit substantially free of pathogenic organisms such as fungi and sapsucking insects are provided together with a method to biocontrol pathogen infestations on plants using flavonoid and aromatic aldehydes. By "biocontrol" is intended control of plant pathogens via direct antipathogenic activity and/or induced resistance of the host plant to pathogen infestation. A fungus and/or insect colonizing surface of a plant part such as a leaf, root, or flower part, or a tissue such as xylem or phloem, is contacted with a natural product. By "colonizing" is intended association of a microorganism or insect with a plant part or tissue from which the pathogen derives nutrients, typically essential nutrients such as amino acids, particularly methionine. By "natural product" is intended an organic compound of natural origin that is unique to one organism, or common to a small number of closely related organisms, and includes secondary metabolites of fungi and chemicals produced by plants. The natural products can be isolated from a natural source, be wholly or partly synthetic, or be produced by recombinant techniques.

The method of the subject invention is carried out by adding an effective pathogen-inhibiting amount of a compound of the invention to a plant host or to the substrate in which it is growing or is to be growing. The amount of antipathogenic agent that is applied either to the plant itself or to the rhizosphere will depend upon the degree of infestation and to some extent upon the formulation and the specific compounding used and therefore must be empirically determined for best results. By "antipathogenic" is intended a pesticide, i.e. a formulation which is effective for controlling the growth of pathogens and can involve killing the pathogen and/or slowing or arresting its proliferation. Pathogens include insects, fungi and other microorganisms which negatively affect the plants which they colonize.

The compositions and methods of the subject invention offer several advantages over existing compositions and methods. Although a flavonoid aldehyde, cinnamic aldehyde, has been reported to exhibit antifungal properties, it has not previously been used on plants in the absence of an anti-oxidant. As an example, U.S. patent application Ser. No. 4,978,686, discloses that an antioxidant is required for use with cinnamic aldehyde for a composition which is used for application to crops. Anti-oxidants are expensive, accordingly significant cost benefits are realized with the subject formulation. In addition, a single application of cinnamic aldehyde is sufficient for long term protection of the plant host from pathogenic organisms, including both rust and powdery mildew, and is effective at lower concentrations than has been reported previously. Phytotoxicity of the formulation also is decreased due to the lower concentrations of aldehyde which are used. The long term control of pathogenic organisms results in a healthier plant and an improved yield of produce by the host plant as compared to untreated plants; the lower concentrations and single dose of antipathogenic agents decrease the likelihood of damage to the plant or its crop as well as decrease the likelihood of any adverse side effects to workers applying the pesticide, or to animals, fish or fowl which ingest the tissues or parts of treated plants.

More and more pesticides are not being re-registered by public regulatory agencies. For example, the Delaney clause has recently put into question the future of many pesticides. With limited pesticide availability, certain applications, such as the treatment of phylloxera on grape roots where translocation is important in the treatment and control of the insect pest and related fungal pathogens, will be problematic.

The subject formulations also provide for effective control of both fungi and insects, eliminating the need for application of multiple agents. In particular situations, such as where an insect damages a plant part or tissue and a secondary fungal disease develops, this aspect of the invention is particularly advantageous. The subject formulation is as shown in formula (1) above. A preferred formulation is shown in formula (2) below:

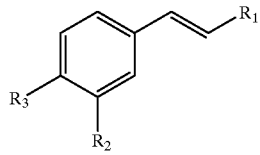

(2)

wherein $R_1$ represents —CHO, $R_3$ represents —H—OH or an organic substituent containing from 1 to 10 carbon atoms and from 0 to 5 heteroatoms; and $R_2$ represents —H a methoxy group or organic substituent containing from 1 to 10 carbon atoms, and from 0 to 5 heteroatoms. Of particular interest are aromatic aldehydes. Examples of aromatic aldehydes of use in the present invention are cinnamic aldehyde ((3) below):

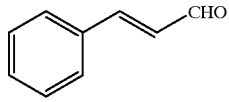

(3)

and coniferyl aldehyde ((4) below):

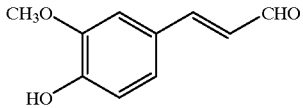

(4)

A number of the aromatic and aliphatic aldehydes which find use in the subject invention, such as benaldehyde, acetaldehyde, cinnamaldehyde, piperonal, and vanillin are generally regarded as safe (GRAS) synthetic flavoring agents (21 CFR §172.515). These compounds have been reported to have inhibitory activity against *C. botulinum* spore germination. Bowles and Miller, G. *Food Protection* (1993) 56:788–794. The general formula of these compounds is shown above as (1).

The aromatic and aliphatic aldehydes of the subject invention may be prepared by various synthetic methods known to those skilled in the art. For example, see, J. March, ed., Appendix B, *Advanced Organic Chemistry: Reactions, Mechanisms, and Structure,* 2nd Ed., McGraw-Hill, New York, 1977. Cinnamaldehyde may be prepared synthetically, for example, by oxidation of cinnamyl alcohol (Traynelis et al., *J. Am. Chem. Soc.* (1964) 86:298) or by condensation of styrene with formylmethylaniline (Brit. patent 504,125). The subject aldehydes may also be obtained by isolation from natal sources. For example, cinnamaldehyde may be isolated from woodrotting fungus, *Stereum subpileatum*. Birkinshaw et al., *Biochem. J.* (1957) 66:188.

The compounds may be used either alone or in combination with other active or inactive substances and may be applied by spraying, pouring, dipping, in the form of concentrated liquids, solutions, suspensions, powders and the like, containing such concentration of the active compound as is most suited for a particular purpose at hand. They may be applied, for example, in the form of dilute solution, in a suitable solvent directly to the rhizosphere either as part of an irrigation schedule or as a separate application. For use as a foliar spray, although the aldehyde can be formulated alone, it can be rendered substantive by including an emulsifier such as Tween 80. Other detergents which can be used include anionic detergents such as those described in U.S. patent application Ser. No. 4,978,686. Other compounds which can be used alone or in conjunction with detergents to increase the substantive properties of the formulation include saponins from any of a variety of sources. Generally, detergents and other agents used in the formulation do not detract from the pesticide properties of the aromatic aldehydes but do increase the substantive properties of the formulation (see for example, U.S. patent application Ser. No. 4,477,361) and may improve the pesticide properties (see below). Additional components such as an aqueous preparation of a salt of a polyprotic acid such as sodium bicarbonate, sodium sulfate, sodium phosphate or sodium biphosphate can be included in the formulation, to increase the antifungal properties of the formulation. The resulting emulsion is diluted to an appropriate concentration for use.

In a preferred embodiment, the formulation includes cinnamic aldehyde and/or coniferyl aldehyde in a formulation containing Tween 80 as an emulsifier and sodium bicarbonate. The preferred formulation for treating powdery mildew, rust and spores, as well as aphids is an emulsion which contains cinnamic aldehyde and/or coniferyl aldehyde, 0.001% to 10% by weight, the salt of a polyprotic acid, 4% to 12% by weight, an emulsifier 2% to 4%, and the balance water. Generally, the total amount of aldehyde(s) present in the formulation is 5% or less. The formulations are effective and stable without the use of antioxidants, although particular aldehydes may have inherent antioxidant properties, for example, coniferyl aldehyde. Stability of the formulation can be evaluated by a variety of methods, including accelerated tests in which a formulation of interest is exposed to elevated temperatures over a set time. Samples of the formulations are taken at regular intervals and analyzed chemically by methods known to those skilled in the art to determine the rate and nature of degradation.

The most effective amount for compositions including compounds of formula (3) and/or formula (4) as well as the amount of other compounds of formula (1) which may find use can be determined using protocols such as those described in the Examples. Generally, an effective growth modulating amount of one or more compounds of formula (2) is 0.01 g/l to 25 g/l. These protocols also can be used to optimize each formulation for specific pathogens using any of the compounds encompassed by formula (1) as well as for use on specific plants to minimize phytotoxicity while maximizing the antipathogenic effect of the formulation.

In some instances, the efficacy of the formulation can be increased by adding one or more other components, i.e., a compound other than a compound of formula (1), to the formulation where it is desirable to alter particular aspects of the formulation. As an example, it may be desirable for certain applications to decrease the phytotoxicity effect (phytotoxicity rating of 2 or less, with 1 or less preferred, below) or to increase the antipathogenic effect of the formulation (mean disease resistance of 60% or better, with a least about 70% or greater preferred, see below) or both. It is preferable that the additional component(s) minimize phytotoxicity while increasing the antipathogenic effect of the formulation. Of particular interest is the use of a component(s) which is a synergist to increase the mean disease resistance while minimizing the phytotoxic effect as related to a particular formulation. By "synergist" is intended a component which, by virtue of its presence, increases the desired effect by more than an additive amount. The concentration of one or more of the other formulation ingredients can be modified while preserving or enhancing the desired phytotoxic and antipathogenic effect of the formulation. Of particular interest is the addition of components to a formulation to allow for a reduction in the concentration of one or more other ingredients in a given formulation while substantially maintaining efficacy of the formulation. Combination of such a component with other ingredients of the formulation can be accomplished in one or more steps at any suitable stage of mixing and/or application.

Preferred additional components include saponins. Saponins are a class of compounds, each consisting of a sapogenin portion and a sugar moiety. The sapogenin may be a steroid or a triterpene and the sugar moiety may be glucose, galactose, a pentose, or a methylpentose. S. Budavari, ed., *The Merck Index*, 11th ed., Merck & Co., Inc., Rahway, N.J., 1990, p. 1328. The saponins for use in the present invention can be produced and/or isolated from various plant parts including fruit, leaf, seed and/or root, using means known in the art, from a variety of sources including the various plants known to produce them, ranging from yucca, quillaja, agave, tobacco, licorice, soybean, ginseng and asparagus to aloe woods. Saponins for use with the present invention are preferably non-toxic to humans and higher animals. Most preferably the saponin for use in the present invention is non-toxic food grade, the source being from yucca plants. Even more preferred are the saponins from *Yucca schidigera* or *Y. valida* and their equivalents. The saponins are generally prepared by a cold press extrusion process and the resulting liquid extract analyzed by HPLC for saponin concentration. The yucca fiber also can be used; it is typically sundried, mulled and sized by screening.

A variety of rally related saponins are known, the most variable structural feature being the glycosylation pattern. Saponins also may contain additional modifications, such as the sarasaponins which are saponins with a steroid attached, and saponin structure can be modified by any number of enzymatic, chemical and/or mechanical means known in the art. Nobel, Park S., *Agaves*, Oxford Univ. Press, New York, 1994, pp. 42–44. Accordingly, derivatives of these compounds which produce a formulation having the desired antipathogenic and/or phytotoxic effect are considered equivalents of the invention. Depending on its structure, a given saponin can have a particular pesticidal property and lend use with the present formulations.

Generally an effective amount of saponin is of the range 0.01 to 0.1% and most preferably about 0.01% v/v aqueous solution of 10° brix saponin extract.

For applications where the formulation is to be used to prepare the ground or other growth substrate for planting of host plants susceptible to particular pathogens, or to apply to an already infested growth substrate, the formulations of the subject invention can be added directly to the rhizosphere or the substrate or they can be bound to a solid support or encapsulated in a time release material. Where a solid carrier is used, materials which can lead to oxidation of the active aldehydes should be avoided. Examples of delivery systems which can be used include starch-dextran, and the like. See Yuan et al., *Fundamentals and Applied Toxicology* (1993) 20:83–87 for other examples of appropriate materials.

In addition to the specific compounds of the formulas (1), (2), (3) and (4) set forth above, derivatives of any of these compounds that produce a compound of the formula identified above upon action of a biological system on the derivative are considered to be equivalent to compounds of the invention. Thus application of precursor compounds to plant parts or tissues would be equivalent to the practice of the present invention. Biological conversion of precursor compounds into aromatic aldehydes is described in, for example, U.S. patent application Ser. No. 5,149,715 and references cited therein. So also Casey and Dobb *Enzyme Microb. Technol.* (1992) 14:739–747.

The method of the present invention is carried out by introducing into a target pathogenic organism a sufficient amount of an anti-pathogenic agent to impair growth and/or viability of the target pathogenic organism. A formulation containing the antipathogenic agent is introduced to a plant tissue or part. For example, the formulation is sprayed on, as a wet or dry formulation, the surface and/or underside of the leaves or other plant tissue or part of a plant infected with a plant pathogen, or of a plant susceptible to infestation with a plant pathogen, preferably to the point of run off when a wet formulation is used a plant growth promotant, such as saponin, is optionally used either in the antipathogenic formulation or as a separate formulation. Alternately, the formulation can be applied wet or dry to the rhizosphere where it can contact the roots and associated pathogenic organisms which colonize the roots. In some instances, time-release formulations may find use, particularly for applications to the rhizosphere.

The method of introducing into the target organism can be by direct ingestion by the pathogenic organism, for example, an insect or a fungus, from a treated plant surface, or by feeding of a pathogenic organism on a nutrient-providing surface of a host entity which is colonized by the target pathogenic organism which either contains or has on its surface the antipathogenic agent. The presence of the antipathogenic agent on a nutrient-providing surface of a host plant can be a result of direct contact of the anti-pathogenic agent with the plant part or it can be by elaboration from the host plant as a result of induction of systemic resistance as a secondary effect to prior treatment of the plant with the anti-pathogenic agent, or as a result of genetic modification of the host plant.

A preferred method for producing a desired component of the present formulations in a plant host is through recombinant DNA means. Particularly by modifying the level of at least one compound of interest of the formula (1), (2), (3), (4) and/or saponin in plant tissues of interest through construction of transgenic plants using recombinant techniques known in the art. The methods involve transforming a plant cell of interest with an expression cassette functional in a plant cell comprising as operably linked components in the 5' to 3' direction of transcription, a transcriptional and translational initiation regulatory region, joined in reading frame 5' to a DNA sequence encoding and capable of modulating the production and/or required to produce the compound of interest, and translational and transcriptional termination regions. Expression of an enzyme required to produce the compound of interest provides for an increase in production of the compound as a result of altered concentrations of the enzymes involved in the compounds' biosynthesis.

One or more compounds of the present formulations can be introduced to the target organism by modulating the expression of one or more genes a gene encoding or more enzymes or an enzyme pathway or cluster required to control the level of the compound of interest in a plant, plant part, plant cell, specific plant tissue and/or associated with a particular stage of plant growth. The enzyme or enzymes can be in a biosynthetic pathway or a degradation pathway and the regulation will be up or down respectively; i.e., to modulate expression of an indigenous or an endogenous plant gene an indigenous plant gene is one which is native to the genome of the host plant. An endogenous plant gene is one that is present in the genome of the plant host of interest, and may be an indigenous gene or a gene that is present as a result of infection of the plant A, a viral gene), or otherwise naturally incorporated into the plant genome. The host plant also can be modified by recombinant means or by traditional plant breeding methods to introduce one or more genes exogenous to the host plant which encode enzymes which control the level of the compound of interest and/or are in the synthetic pathway for one or more compounds of formula (1), (2), (3) or (4) and/or saponin. By "modulation of gene expression" it is intended control of production of a gene product of interest at the level of transcription, translation and/or post translation. The level of the compound of interest is controlled by modulating the expression of one or more endogenous genes or transgenes encoding one or more enzymes required to synthesize the compound of interest.

Methods for modulating gene expression in plants are known in the art. Variation in growth conditions or exogenous application of compounds to a plant can affect gene expression. For example, the formulations of the present invention can be used to induce systemic plant resistance through modulation of endogenous gene expression. At the molecular level, gene expression depends substantially on the transcription, translation and termination control regions which regulate expression of a structural gene coding region. By exploiting the plant signals which regulate these control regions or by the direct recombinant manipulation of the control regions, expression of a gene encoding an enzyme required to control the level of cinnamic aldehyde, for example, can be modulated. For use in a transgene supplied exogenously to a plant host, the transgene will include control regions that are selected and designed to achieve the desired level and timing of gene expression. As appropriate, the control regions may be homologous (native) or non-homologous (non-native) to the gene of interest. By "homologous" it is meant that the control region(s) is from or substantially similar to a control region normally associated with the gene of interest. By "non-homologous" it is meant that the control region(s) originates from a different nucleotide source or sequence or is substantially different from the control region(s) normally associated with the gene of interest. For example, if the enzyme coding sequence is non-homologous in source as compared to the control regions, in order to have expression of the gene in a plant cell of interest, transcriptional and translational initiation regulatory regions or promoters functional in these plant cells must be provided operably linked to the coding sequence. Transcription and translation initiation signals functional in plant cells include those from genes which are present in the plant host or other plant species, and direct constitutive or selective expression in a plant host.

DNA constructs for expressing a gene of interest are prepared which provide for integration of the expression cassette into the genome of a plant host. Integration can be accomplished using transformation systems known in the art such as Agrobacterium, electroporation or high-velocity microparticle-mediated transformation. For biosynthesis of cinnamic and/or coniferyl aldehyde, plant cells are transformed with an expression cassette comprising DNA encoding a structural gene for one or more enzymes required to synthesize cinnamic and/or coniferyl aldehyde and capable of increasing the amount of these aldehydes in the tissue of interest. Of particular interest are those genes encoding one or more enzymes capable of metabolizing a precursor compound required for the biosynthesis of the saponin, cinnamic and/or coniferyl aldehyde compound of interest from substrates normally found in a plant cell. Similarly, for saponin biosynthesis, plant cells are transformed with an expression cassette comprising DNA encoding a structural gene for one or more Ames required to synthesize saponin.

Depending upon the application, cinnamic aldehyde, saponin or one of the other compounds of interest can be preferentially expressed in a tissue of interest and/or a particular organelle. Of particular interest is the selective control of cinnamic and/or coniferyl aldehyde production and/or saponin in plant tissues such as leaves, roots, fruits and seeds; the tissue site can be varied depending upon the site of infestation of the target pathogen. Tissue specificity is accomplished by the use of transcriptional regulatory regions having the desired expression profile. Translocation of the enzyme to a particular organelle is accomplished by the use of an appropriate translocation peptide. Methods for tissue and organelle specific expression of DNA constructs have been described are known in the art ([refs]). For example, promoters showing differential expression patterns in fruit are described in U.S. Pat. No. 4,943,674 and U.S. Pat. No. 5,175,095; in seed in U.S. Pat. No. 5,315,001; in rapidly developing tissues and tender shoots in U.S. Pat. No. 5,177,011.

To verify regulation and expression of the gene of interest, various techniques exist for determining whether the desired DNA sequences present in the plant cell are integrated into the genome and are being transcribed. Techniques such as the Northern blot can be employed for detecting messenger RNA which codes for the desired enzyme. Expression can further be detected by assaying for enzyme activity or immunoassay for the protein product. Most preferably the level of the compound of interest present in a plant host is measured using methods known in the art ([refs]). A desired phenotype, for example, is increased cinnamic aldehyde content in a plant tissue of interest as measured by expression of the gene of interest and/or the level of cinnamic aldehyde present in the plant host as compared to a control (non-transgenic) plant.

For introduction of one or more compounds of the present formulations to the target organism, a plant host expressing a gene encoding an enzyme required to control the level of the compound of interest results in the exposure of a target organism to at least one component of the antipathogenic formulation. In another embodiment, selective expression of the gene of interest provides for systemic plant host resistance to pathogen attack or colonization. At least one component of the antipathogenic formation can be expressed by the transgenic plant host and optionally other components of the antipathetic formulation are exogenously applied to the plant host so that the combination elicits the desired antipathogenic effect when either directly or indirectly introduced to the target organism.

Transgenic plants having an increased ability to accumulate aromatic aldehydes such as cinnamaldehyde and coniferyl aldehyde to provide self-protection against plant pathogens or be used as a natural source of aromatic aldehydes for extraction and subsequent use as a chemical pesticide can be prepared.

Accumulation of aromatic aldehydes can be achieved by downregulating the expression of specific plant genes that encode enzymes which either cause further metabolism of the desired aldehydes or divert metabolic intermediates away from the desired aldehydes. In the case of cinnamaldehyde, for example, this involves downregulating the expression of cinnamate 4-hydroxylase (CA4H) and cinnamic alcohol dehydrogenase (CAD). By reference to FIG. 7, it can be seen that CA4H ordinarily diverts some cinnamic acid away from cinnamaldehyde to produce p-coumaric acid, itself a metabolic intermediate. Reducing CA4H activity alone is not sufficient to cause accumulation of cinnamaldehyde because CAD can rapidly convert cinnamaldehyde to cinnamyl alcohol, which then becomes incorporated into lignin or accumulates as glycosides. Simultaneously reducing both CA4H and CAD activities results in increased metabolic flux from cinnamic acid into cinnamaldehyde and decreased conversion of cinnamaldehyde into cinnamyl alcohol. Some cinnamaldehyde becomes incorporated into lignin but cinnamaldehyde (either free or as glycosides) also accumulates to above-normal levels, particularly at times when the biosynthesis of cinnamic acid is elevated. This occurs when the level of phenylalanine ammonia lyase (PAL; the first and rate-limiting step in general phenylpropanoid metabolism, Hahlbrock and Scheel (1989) *Annu. Rev. Plant Physiol. Plant Mol. Biol.* 40:347–369) activity is high, a situation that naturally occurs in plants in response to a wide range of stimuli including invasion by fungal pathogens and mechanical damage associated with wounding and insect feeding.

Inhibiting CAD activity in transgenic plants has been proposed as a method of reducing lignin synthesis in plants and thereby improving the digestibility of fodder crops (WO 93/05159). These experiments suggested that lignin biosynthesis had been altered qualitatively, but not necessarily quantitatively, but did not demonstrate or appreciate the desirability of accumulating cinnamaldehyde as a method of increasing protection against pathogens.

A number of plant CA4H and CAD genes have been cloned and their sequences are available from GenBank. Portions of these genes that include nucleotide sequences that are conserved between different plant species can be used directly in a plant expression vector (antisense or sense orientation) to suppress the expression of the corresponding endogenous genes (e.g., Pear, et al., *The Plant Cell Antisense Res. and Develop.* (1993) 3:181–190, Napoli, et al., *The Plant Cell* (1990) 2:279–289. More preferably, these conserved gene sequences are used to isolate CA4H and CAD cDNA clones from a cDNA library of the plant species that is to be modified. The resulting cDNA clones, or portions thereof, are then introduced into a plant expression vector (antisense or sense) and used to transform the plant(s) of interest. DNA constructs according to the invention preferably comprise a sequence of at least 50 bases which is homologous to the endogenous CA4H or CAD genes.

A recombinant DNA molecule can be produced by operatively linking a vector to a useful DNA segment to form a plasmid that can be used for plant transformation. A vector capable of directing the expression of RNA from a cloned portion of a gene is referred to herein as an "expression vector." Such expression vectors contain expression control elements including a promoter. Typical vectors useful for expression of genes in higher plants are well known in the art and include vectors derived from the Ti plasmid of *Agrobacterium tumefaciens* described by Rogers et al., *Methods in Enzymology* (1987) 153:253–277. A common promoter that is used to provide strong constitutive expression of an introduced gene is the cauliflower mosaic virus (CaMV) 35 S promoter (available from Pharmacia, Piscataway, N.J.). Either constitutive promoters (such as CaMV 35S) or inducible or developmentally regulated promoters (such as the promoter from a PAL gene or the endogenous CA4H or CAD genes) can be used. Use of a constitutive promoter will tend to affect functions in all parts of the plant, while use of an inducible or developmentally regulated promoter has the advantage that the antisense or sense RNA is only produced in the tissue and under the conditions it is required. The use of developmentally regulated promoters is preferred in the use of this invention because the down-regulation of phenylpropanoid biosynthesis is known to be capable of producing undesirable side-effects on the development of transgenic plants containing a heterologous PAL gene (Elkind, Y. et al., 1990) *Proc. Nat. Acad. Sci.* (1990) 87:9057–9061.

A number of different transformation methods are available for the routine transformation of a wide range of plant species. One method that is particularly efficient for the transfer of DNA into dicotyledonous plants involves the use of Agrobacterium. In this method the gene of interest is inserted between the borders of the T-DNA region that have been spliced into a small recombinant plasmid with a selectable marker gene (for example encoding neomycin phosphotransferase II or phosphinothricin acetyltransferase). The recombinant plasmid is then introduced into an Agrobacterium host by transformation or triparental mating. The Agrobacterium strain carrying the gene(s) of interest is then used to transform plant tissue by co-culturing the bacteria with an appropriate plant tissue (e.g., leaf disc). Transformed cells are selected in tissue culture using the appropriate selection agent and plants are then regenerated (see Horsch, R. B. et al., *Science* (1985) 227:1229–1231. Other methods that have been used in the transformation of plant cells, and in particular the more recalcitrant crop plants, include biolistics and electroporation (for detailed protocols, see Sanford, et al., (1993) *Methods in Enzymology* 217:483–509; and Potter, (1993) *Methods in Enzymology* 217:461–478.

Once transgenic plants have been produced, conventional enzyme assays for CA4H and CAD are used to determine the level of suppression of enzyme activity achieved in different transformants. It is likely that only a small fraction of the transformants produced will have a sufficiently low residual enzyme activity to cause the accumulation of aromatic aldehydes without also producing some undesirable side-effects on plant development. For this reason, a preferred method of producing the desired transformants with both CA4H and CAD suppressed is to introduce the two genes separately into different transformants and then combine them by standard sexual crosses. This permits a larger number of combinations of level of gene suppression to be evaluated at the same time.

An alternative to overproducing aromatic aldehydes in transgenic plants is to use the plant genes to confer on a microbial host the capability of synthesizing specific aromatic aldehydes. The resulting microbes may be used either to produce the flavonoid aldehydes in a fermentation system or as a natural delivery system of the aromatic aldehydes in viable or non-viable microbial preparations. Yeasts, especially *Saachoromyces cerevisiae*, are preferred organisms for this purpose because they have already been engineered for high-level expression of PAL (Faulkener, J. D. B. et al., *Gene* 143:13020, 1994) and a plant cinnamate 4-hydroxylase has been shown to function in yeast (Urban, et al. 1994 *Eur. J. Biochem* 222:843–850.

The expression of PAL introduces the capability to produce cinammic acid from phenylalanine. Two additional enzymic steps are required to produce cinnamaldehyde from phenylalanine. In plants, these steps are catalyzed by the enzymes cinnamate:CoA ligase (CL) and cinnamoylCoA reductase (CCoAR) but as 4-coumarateCoA ligase (4CL) can also use cinnamic acid as substance (Knobloch, and Hahlbrock 1977, *Arch. Biochem. Biophys.* 184:237–248, 4Cl can be used instead of CL. More than 20 cloned PAL genes and more than 6 4CL genes have been described in sufficient detail (GenBank) to facilitate their use in practicing the current invention. A gene for a CCoAR is obtained by applying standard gene cloning techniques to isolate a cDNA clone using as a probe sequence derived from the amino acid sequence of the N-terminus, or peptide fragments, of the purified protein. CCoAR has been purified and partially characterized from soybean cultures (Wengenmayer et al., (1976) *Eur. J. Biochem,* 65:529–536; Luderitz, and Grisebach, *Eur. J. Biochem,* 119:115–124, 1981), spruce cambial sap (Luderitz, and Grisebach, supra), poplar xylem (Sarni, et al., *Eur. J. Biochem,* 139:259–265, 1984) and differentiating xylem of *Eucalyptus gunnii* (Goffner, et al., *Plant Physiol.* 106:625–632, 1994). The preferred method of purification is that of Goffner et al. (supra) because it results in a single protein band on SDS-polyacrylamide gels that an be used for protein sequencing.

The cloned genes are introduced into standard expression vectors and used to transform a microbial host, preferably yeast, by standard transformation techniques such as electroporation (Becker, and Guarante, *Methods in Enymol,* 194:182–187, 1991). Standard enzyme assays are used to confirm the functional expression of the engineered genes and assays for aromatic aldehydes are used to select stains with maximal production. Because aromatic aldehydes have antimicrobial properties it is preferred to use expression vectors that will cause expression of the introduced genes only late in the growth cycle or in response to a chemical inducer. It may also be desirable to grow the engineered microbia host in an immobilized whole cell reactor (e.g., Evans, et al., *Biotechnology and Bioengineering* 30:1067–1072, 1987) to prevent the aldehydes from accumulating in the culture medium.

The target pathogenic organisms include fungi which colonize a surface of a part of a plant which is an elicitor for the fungus. By elicitor is intended that the plant secretes nutrients required by the fungus. Examples of fungi and the plant parts which the colonize are as follows. Black spot on fruit; *Fusarium sp.* on flowers roots and leaves; and *Fusarium spp.* and aspergillus on roots and leaves. Fusarium causes vascular wilts of annual vegetables and flowers, herbaceous perennial ornamentals, plantation crops and the mimosa tree. Different plants are attacked by special forms or races of the fungus. Verticulum (*V. albo-atrium* and *V. dahlise*) cause vascular wilts and colonize roots, flowers and leaves. In addition the following also constitute target organisms: *Phragmidium spt; Diplocaopan rosae; Sphaerotheca tannosa; Oibiapsis sicula; Phytophoya taraesitica; Puccinia spp; Alternaria sp; Susaiun spp; Botrytis cinera; Sclerotinia Homoeocarca*; Dutch Elm disease (*Ceratocystis ulmi*) and oak wilt (*C. fagacearum*). Ceratocystis causes vascular wilts, mainly of trees.

Target organisms also include insects, particularly those of the orders Orthoptera; Thysanoptera which includes hips; and Homoptera which include aphids, leafhoppers, white flies, mealy bugs, cicadas and scale insects. It is a theory of the invention that the insects which are susceptible to treatment with the subject formulations are those which harbor symbiotic bacteria in their gut. Accordingly, insects other than those listed which harbor symbiotic material also can be controlled with the subject formulations. Other target organisms include arachnids, particularly spider mites (arthropoda).

Plants which are of interest for treatment are those which are colonized by pathogenic organisms and include flowering plants, grasses, including bent grass, vegetables, cereals and fruits including tomato, potato, artichoke, strawberries, corn, cereal grains, onion, cucumber, lettuce, tobacco, and citrus such as orange, lemons, limes and grapefruit, as well as bell peers and grapes, and fruit trees such as peach, apple and cherry, ornamentals such as roses and trees, particularly conifers. Also included are crops intended for consumption by fish, fowl and animals, including humans, directly or indirectly. By "directly or indirectly" is intended that the crops could be ingested, for example, by humans (direct consumption), or that it is the nonhuman animal or fowl which ingests the crop and is in turn ingested by humans (indirect consumption). Crops intended for consumption include tobacco, fish, animal and fowl fodder, crops intended for processing into alcohol or food products such as corn syrup, and the like.

Of particular interest is treatment of plants affected by powdery mildew which is caused by target organs which are species of fungi of the family Erysiphaceae. Generally the genera are distinguished from each other by the number (one as opposed to several) of asci per cleistotheciun and by the morphology of hypal appendages growing out of the walls of the creistothecium. As an example the following genera cause powdery mildew in the indicated plants: *Erysiphe cichoracearum*, begonia, chrysanthemum, cosmos, cucurbits, dahlia, flax, lettuce and zinnia; *E. graminis*, with cereals and grasses; *E. polgoni*, beans, soybeans, clovers, and other legumes, beets, cabbage and other crucifers, cucumber and cantaloupe, delphinium and hydrangea; *Microsphaera alni*, blueberry, catalpa, elm, lilac, oak, rhododendron, and sweet pea; *Phyllactinia sp. catalpa*, elm, maple and oak; *Podosphaera leucotricha*, apple, pear and quince; *P. oxyacanthae*, apricot, cherry, peach and plum; *Spaelrotheca macularis*, strawberies; *S. mors-uvae*, gooseberry and currant; *S. pannosa*, peach and rose; and *Uncinula necator*, grape, horse chestnut and linden.

Also of particular interest is the treatment of plants affected by rust caused by Basidiomycetes of the order Uredinales. These plant rusts are among the most destructive of plant diseases. They have caused famines and ruined the economics of large areas, including entire countries. There are about 4,000 species of rust fungi. The most important rust fungi and the diseases they cause follow: Puccinia, causing severe and often catastrophic diseases on numerous hosts such as the stem rust of wheat and all other small grains (*P. graminis*); yellow or stripe rust of wheat, barley and rye (*P. striiformis*); leaf or brown rust of wheat and rye (*P. recondita*); leaf or brown drarf rust of barley (*P. hordei*); crown rust of oats (*P. coronata*); corn rust (*P. sorghi*); southern or tropical corn rust (*P. polysora*) sorghum rust (*P. purpurea*); and sugarcane rusts (*P. sacchari* and *P. kuehnii*).

Puccinia also causes severe rust diseases on field crops such as cotton (*P. stakmanii*); vegetables such as asparagus (*P. asparagi*); and flowers such as chrysanthemum (*P. chrysanthemi*), hollyhock (*P. malvacearum*), and snapdragon (*P. antirrhini*). Gymnosporangium, causes the important cedar-apple rust (*G. juniperi-virginianae*) and hawthorn-cedar rust (*G. globosum*). Hemileia, causes the devastating coffee leaf rust. (*H. vastatrix*). Phragmidium, causes rust on roses and yellow rust on raspberry.

Uromyces: several species cause the rusts of legumes (bean, broad bean, and pea) and one causing rust of carnation (*U. caryophyllinus*). Cronartium, causes several severe rusts of pines, oaks, and other hosts, such as the white pine blister rust (*C. ribicola*); fusiform rust of pines and oaks (*C. quercuum f. sp. fusiforme*); eastern gall or pined rust (*C. quercuum f. sp. virginianae*); pine-sweet fern blister rust (*C. comptoniae*); pine-Comandra rust (*C. comandrae*); and southern cone rust (*C. strobilinum*). Melampsora, causes rust of flax (*M. lini*). Coleosporium, causes blister rust of pine needles (*C. asterinum*). Gymnoconia, causes orange rust of blackberry and raspberry. Phakopsora, causes the potentially catastrophic soybean rust (*P. pahyrhizi*). Tranzschelia, causes rust of peach.

For treatment of powdery mildew, rust and other pathogens which colonize the leaves of the host plant, the host plants are sprayed to run off with a formulation of the invention. The amount of compound(s) of formula (1) used will vary depending in part upon the target pathogen and the host plant and can be determined empirically by evaluating the sensitivity of the target organism to the formulation and the phytotoxic effects of that formulation or the host plant. The plants can be sprayed prior to or after infestation, preferably prior to infestation. However, in order to minimize damage to the host plant, where feasible, it is preferable to treat older plants, as young green leaves tend to be more susceptible to phytotoxicity. Alternatively, transgenic crops can be used, which express one or more components of the formulation in an amount sufficient to inhibit growth of the pathogen and/or kill the pathogen. Preferably the component(s) is expressed in the tissue colonized by the pathogen, for example the leaves.

Also of particular interest is treatment of phylloxera infestation in grapes. For this application, it is necessary to deliver the formulation to the roots of the plant to the location of the insect colony. Typically, phylloxera are found as deep as the roots of the host plant, which may be eight feet or deeper. When used in a solid form or microencapsulated, the dosage used is typically on the order of 1% to 35% on a w/w basis, the maximum loading to be determined as a function of shell material selected. Analytical chemical techniques are used to determine and optimize rate of release. For qualitative purposes GC techniques can be used to determine the amount of aldehyde released. The samples of encapsulated (pelletized) product are mixed with the soil types selected and sampled at different time periods to measure release. Alternatively, volatile gases released from the formulation can also be analyzed. For measuring the activity of foliar and drip irrigation applications the stability of the formulations over time can also be evaluated using the GC methodology using methods known to those skilled in the art. Methanol or alcohol extractions of the formulations also can be prepared for HPLC analysis. The aldehyde components can be coupled to a solid support, optionally through a linker such as a polysaccharidase binding domain, where the solid support is a polysaccharide such as cellulose, particularly microcrystaline cellulose. The preparation of cellulose binding domains is described in U.S. patent application Ser. Nos. 5,340,731; 5,202,247 and 5,166,317. The aldehydes can be coupled to the binding domains, with or without a cleavable bond, using methods well known to those skilled in the art. As in the case of treatment of powdery mildew and rust, transgenic crops can be used; for treatment of phylloxera the preferred tissue of expression of components of formula (1) is the root.

In addition to treating a host plant, seeds can also be treated using the subject formulations. The seeds can be dusted with a powder preparation (see U.S. patent application Ser. No. 4,978,686 for examples of inorganic materials to which the formulations can be adsorbed) or admixed in a plant substrate such as vermiculite. Seeds also can be obtained from transgenic crops, wherein the components of formula (1) have been expressed in seed, preferably preferentially in seed. Seedlings grown under sterile conditions from treated seeds are free of susceptible fungi and insects. Additionally, seedlings also can be treated with the subject formulations. In some instances it may be necessary to adjust the treatment formulation so as to reduce any phytotoxicity associated with the treatment as tender young shoots are more likely to exhibit phytotoxicity symptoms.

In order to determine the susceptibility of particular fungi or insects to the claimed compositions, in vitro and in vivo tests ]mown to those skilled in the art are used. The mean disease control can be calculated for particular pathogens on particular host plants. Generally it is desirable to obtain a mean disease resistance of 60% or better, preferably at least about 70%. The formulations also need to be evaluated for phytotoxicity; it therefore is important that at least one evaluation of the toxicity of the formulations be on living plants of the host variety. Phytotoxicity can be rated as follows in order of increasing severity of toxicity: 0-plants without any symptoms; 1-very slightly browning of hypocotyl (no other symptoms); 2-some wilting of plant, dying of lower leaves, some browning of vascular system; 3-wilting of entire plant, leaves dying, hypocotyl with external and internal symptoms; 4-necrosis of stem, plant dying. It is preferable that the formulation used have a phytotoxicity rating of 2 or less, more preferably 1 or less.

The components of a formulation to be used for a particular application can be determined by constructing a dose response curve by evaluating first the concentration range over which a given component has no activity to where it provides maximum activity and then evaluating this component separately and in combination the components of interest for a given formulation. As an example, the effects of cinnamic aldehyde in a range from 0.1 ppm to 25,000 ppm on powdery mildew is evaluated. At a dose of 0.05%, it provides 3% mean disease control. The mean disease control can be increased by using higher doses of cinnamic aldehyde, and/or adding other compounds of formula (1), or by increasing the substantiveness of the formulation by adding detergent, and the like. The antipathogenic and/or phytotoxic effect of a particular formulation on a given pathogen and/or plant host is then measured for each formula and component with or without a serial dilutent of any additional component of interest. Optimal dose-ranges are calculated in vitro and in vivo using techniques known to those of ordinary skill in the art. Preferred formulation provide: a mean disease resistance of at least about 60% or better with an optimum of about 70% or greater; and/or a phytotoxicity rating of 2 or less, with 1 or less being optimum.

The following examples are offered by way of illustration and not by way of limitation.

EXAMPLES

Materials and Methods

The chemicals used in the examples given below were obtained from the following sources: cinnamic aldehyde, Spectrum Chemical Company, N.J.; coniferyl aldehyde, APIN Chemical, U.K.; Tween 80 and sodium bicarbonate Spectrum Chemical Company, Gardena, Calif.

Example 1

Treatment of Powdery Mildew on Rose Cultivars

Potted Roses. Eight cultivars of rose were to investigate the effect of a cinnamic aldehyde/NaHCO$_3$ formulation on rust and spores. The cultivars used included Moss unnamed (Moss), Galica, Rosette Delize (Hybrid Tea), Rosa Rugosa Rubra (Rugosa), Abel Morrison (Hybrid perpetual), John Laing, Betty Prior, and Rose de Roi. Five (5) potted cultivars (Moss, Galica, Hybrid Tea, Rugosa, and Hybrid perpetual) were selected and assigned a disease rating after Paulus and Nelson (supra) for powdery mildew, rust and spores.[1] The Moss and Galica cultivars were 5 on a scale of 0–5 (where 0=no powdery mildew rust/spores lesions, 1=1–25, 2=26–50, 3=51–75, 4=76–90, and 5=>90% total leaves per bush). The Hybrid Tea and Hybrid perpetual were rated 3 and the Rugosa was rated 1. The Moss and Galica also were infected with rust equivalent to a 3 rating.

[1]. Spores were evaluated only on Moss, Galica and the control plants.

Each cultivar received a foliar spray of about 100 ml of a cinnamic aldehyde formula containing 5 g cinnamic aldehyde, 80 g NaHCO$_3$, 10 g of Tween 80 and water to 1000 g. In addition, 250 ml of 0.01% (v/v) aqueous solution of 10° brix saponin extract from the yucca shidigera plant was administered to each potted plant once a week beginning with the date of the fist cinnamic aldehyde/NaHCO$_3$ treatment. Control plants received no treatment. A single treatment was eradicative of powdery mildew, rust, and spores though the final weekly field observation eight weeks later as compared to the no treatment controls which remained at disease ratings of 5, 3, and 4 for powdery mildew, rust and spores, lively. Moreover, the treatment appeared to have induced systemic resistance. No phytotoxicity was observed.

Field grown roses. Another experiment was designed for field grown cut flower rose to evaluate the efficacy of powdery mildew control by cinnamic aldehyde/NaHCO$_3$ during the same period (season) and environmental conditions. Powdery mildew and rust inoculum were high in the test field, and no additional inoculum was necessary to provide disease pressure. Cultivars John Laing, Betty Prior, and Rose de Roi were used in tis investigation. Eight John Laing plants from a block row of sixteen were selected for treatment. Every other plant beginning with the first plant in the row was treated. Three Betty Prior plants were selected from a block of six were similarly treated, as were two Rose de Roi plants from a block of four. A single foliar spray treatment (about 100 ml) of a cinnamic aldehyde 5 g, and Tween 80, 10 g and NaHCO$_3$ 80 g and water to 1000 g was applied to each setting of cultivars. Plants were an average of 0.86 m apart. The disease rating was the same as that used to evaluate powdery mildew in containerized cultivars. Controls were untreated plants. Absence of wind and exact spraying protected controls from spray drift. The John Laing cultivars were young, 45day-old plants with a rating of 5 for powdery mildew. The Betty Prior cultivars were older (>240 days), previously sprayed with Eagle (120 days prior) with a rating of 3 for powdery mildew and the Rose de Roi were 240days-old plants with a rating of 2 for powdery mildew and 2 for rust using the same scale as provided above. Induced systemic resistance was determined by observing the number of lesions of powdery mildew and rust produced on each plant after treatment as compared to untreated controls. Weekly reviews were made of the various plants. The effect on growth increase of the treatment regimen was determined at the last field observation of each plant.

With the exception of the untreated controls and three plants of cultivar Betty Prior which had reinfection of powdery mildew with a rating of 3, all plants were free of powdery mildew at the end of the five week trial. No phytotoxicity was observed. All plants had new growth exceeding that of the untreated controls.

The Mean Percentage of Disease Control (MPDC) was calculated for even group of plants. The results were as follows for powdery mildew: John Laing, 98.3%; Betty Prior, 64.3%; Rose de Roi, 100%. The average for all three roses was 90.7% for powdery mildew. Rust was evaluated only on Rose de Roi, and was 85.0%. Effective fungicides for powdery mildew should provide a MPDC of ≧70% under Greenhouse or field conditions, and for rust ≧65%.

Example 2

Treatment of Fungi and Insect on Roses with Coniferyl Aldehyde

Six cultivars of infected rose in dedicated experimental rose gardens were used. Four of Mrs. John Laing (Hybrid perpetual) and two of Marchionese of Londonderry (Hybrid perpetual) were treated with one of two formulations of coniferyl aldehyde. The low dose treatment (T1) was a coniferyl aldehyde, 10 g of Tween 80, 80 g of NaHCO$_3$ and 905 g of H$_2$O for 1000 g of product. The high dose treatment (12) was a coniferyl aldehyde formula comprising of 100 g of coniferyl aldehyde, 20 g Tween 80, 120 g NaHCO$_3$, 760 g H$_2$O for 1000 g of product. See Table 1.

The first two Mrs. John Laing plants (P1 and P2) were assigned a disease rating of 3 for powdery mildew and rust after Paulus and Nelson (supra). Mrs. John Laing plants 3 and 4 (P3 and P4) were assigned a disease rating of 4 and 5 respectively for powdery mildew and rust. P3 and P4 also were infected with aphids, each plant with >35 insects. Both Marchionese of Londonderry (P5 and P6) were rated 5 for powdery mildew and rust after Paulus and Nelson (supra). Two treatment formulae were used for this screen trial. Each plant (P1 through P6) received a ≈100 ml treatment spray of as shown in the Table 1 below. Control plants received no treatment (i.e. they were sprayed with water alone). The change in the rating (PRE-POST) was calculated as the mean percentage of disease control (MPDC). MPDC is defined by the formula:

MPDC is defined by the formula:

$$MPDC = \frac{(MDIC - MDIT)}{MPDC} \times 100$$

and

MDIC=Mean % of disease incidence in untreated controls
MDIT=Mean % of disease incidence in the treatment

TABLE 1

Plant - Treatment/Dose Assignment

| Treatment/Dose | Plant |
|---|---|
| T1 - Low | P1, P4, P6 |
| T2 - High | P2, P3, P5 |

As shown in Table 2 below, both formulas reduced (pre-post treatment change) levels of infection. Both powdery mildew and rust levels of infection were reduced a minimum of one rating category after treatment as compared to plants sprayed with water alone.

TABLE 2

| Plant Treatment/Dose | Low (T1) | | | High (T2) | | |
|---|---|---|---|---|---|---|
| | P1 | P4 | P6 | P2 | P3 | P5 |
| PEST | | | | | | |
| Powdery Mildew Pre | 3 | 3 | 4 | 5 | 5 | 5 |
| Post | 2 | 1 | 1 | 2 | 1 | 1 |
| Change | 1 | 2 | 3 | 3 | 4 | 4 |
| Rust Pre CFU | 3 | 3 | 4 | 5 | 5 | 5 |
| Post CFU | 2 | 1 | 3 | 2 | 1 | 1 |
| Change | 1 | 2 | 1 | 3 | 4 | 4 |
| Aphids Pre # | — | 35 | — | — | ≧35 | — |
| Post # | — | 0 | — | — | — | — |
| Change | — | ≧35 | — | — | ≧35 | — |

Aphids were eliminated from P3 and P4 indicating that the formulas have insecticidal properties. Coniferyl aldehyde, as is cinnamic aldehyde, shared antibiotic properties and may eliminate symbiotic bacteria present in the host insect without which the insect cannot live.

Treatment of Powdery Mildew on Rose

A three treatment experiment with Cinnamic Aldehyde Formula and Components, Coniferyl aldehyde formula and combined Cinnamic and Coniferyl aldehyde formula was evaluated on field grown roses known to be susceptible to powdery mildew. The plants were blocked by variety before fungicide treatments and were randomized as to the plants. Two varieties were used in each of the three experiments described below. In experiment 1, Reichsprasident von Hindenburg (Bourbon) and Oskar Cordel (Hyvrid Perpetual) were used; in experiment 2, Rosa Gallica Officinalis (Apothecary Rose) and Deuil de Paul Fontaine (hybrid Moss) were used. In experiment 3 Comte de Chambord (Portland) and Madame Pierre Oger (Bourbon) were used. Experiment 1 evaluated the effect of cinnamic aldehyde alone and in combination with Tween 80 and/or $NaHCO_3$ components, experiment 2 evaluated the effect of Coniferyl aldehyde, and experiment 3 evaluated a combination of cinnamic aldehyde and coniferyl aldehyde with Tween 80 and/or $NaHCO_3$. Nine treatments were tested in experiment 1, six in experiment 2 and six in experiment 3. See Table 3 for treatment protocol; formula 1 was used for these experiments.

Each plant received a single foliar spray of 100 ml following evaluation of powdery mildew infection (after Paulus and Nelson). The response variable recorded for each plant was the powdery mildew infection rating based on the Paulus/Nelson rating scale. Plants were evaluated on this scale just prior to and four days after treatment. Mean percentage of disease control data indicate that all three combination formulas (i.e. G, M, and Q provided in excess of 70% disease control based on these experiments. See Table 4. Treatment Q was significantly better than all other treatments, including benomyl. Moreover, cinnamic aldehyde, coniferyl aldehyde, Tween 80 and $NaHCO_3$ are used in the food industry and there is likely to be little toxicological risk to the consumer or handler from any horticultural or food crop sprayed in this way. Similarly, as these chemicals leave no toxic residue, there is little chance of any detrimental effect on the wider environment, and their use is likely to be compatible with current biological control methods.

TABLE 3

Treatment Protocol

| Group | Treatment | Ingredient(s) | Amount of treatment ingredient(s)[1] Formula 1 | Formula 2 |
|---|---|---|---|---|
| 1 | A | Cinnamic aldehyde (CNMA) | 5 g | 20 g |
| 1 | B | Tween 80 (T80) | 10 g | 20 g |
| 1 | C | $NaHCO_3$ | 80 g | 60 g |
| 1 | D | CNMA + T80 | 5 g, 10 g | 20 g, 60 g |
| 1 | E | CNMA + $NaHCO_2$ | 5 g, 80 g | 20 g, 60 g |
| 1 | F | $NaHCO_3$ + T80 | 80 g, 10 g | 60 g, 20 g |
| 1 | G | Formula 1 (CNMA) | A = 5, B = 10 g, C = 80 g | A = 20, B = 20, C = 60 g |
| 1,2,3 | H | +Control[2] | per manufacture instructions | R,S,T[2] |
| 1,2,3 | I | −Control | $H_2O$ | $H_2O$ |
| 2 | J | Coniferyl aldehyde (COFA) | 5 g | 20 g |
| 2 | K | COFA + T80 | 5 g, 10 g | 20 g, 20 g |
| 2 | L | COFA + $NaHCO_3$ | 5 g, 80 g | 20 g, 60 g |
| 2 | M | Formula 2 (COFA) | J = 5 g, B = 10 g, C = 80 g | J = 20 g, B = 20 g, C = 60 g |
| 3 | N | CNMA + COFA | 2.5 g, 2.5 g | 10 g, 10 g |
| 3 | O | CNMA + COFA + T80 | 2.5 g, 2.5 g, 10 g | 10 g, 10 g, 10 g |
| 3 | P | CNMA + COFA + $NaHco_3$ | 2.5 g, 2.5 g, 80 g | 10 g, 10 g, 60 g |
| 3 | Q | Formula 3 (CNMA + COFA) | A = 2.5 g, J = 2.5 g, B = 10 g, C = 80 g | A = 10 g, J = 10 g, B = 20 g, C = 60 g |

[1]Balance $H_2O$ to 1000 g
[2]R = Benomyl
 S = Malathion
 T = Lilly Miller SSKB

TABLE 4

Effect of Cinnamic Aldehyde and Coniferyl Aldehyde Formulations on Rose Powdery Mildew

| | Aldehyde | | | |
|---|---|---|---|---|
| Additive Formulation | None | Cinnamic Aldehyde (5 g) | Coniferyl Aldehyde (5 g) | Cinnamic Aldehyde (2.5 g) + Coniferyl Aldehyde (2.5 g) |
| | Mean % Disease Control | | | |
| None | 0% | 50% | 56% | 69% |
| T80 (10 g) | 0% | 44% | 44% | 69% |
| $NaHCO_3$ | 44% | 56% | 44% | 88% |
| T80 + $NaHCO_3$ | 19% | 94% | 81% | 100% |
| Benomyl | 79% | NT | NT | NT |

Example 4

Treatment of Grape Phylloxera with Cinnamic Aldehyde and/or Coniferyl Aldehyde alone and/or with Tween 80 and/or $NaHCO_3$ Feeding Site Location Test Mortality resulting from physiological process disruption is determined by the Adult and Nymphal mortality rent and by the Egg Hatch experiment. After hatching, new insects must secure a verified appropriate feeding site. This activity must be successful if the life cycle of the insect is to continue. Research indicates that approximately 80% of phylloxera mortality occurs during this activity. Low dose concentrations of formulae may be protective of grape stock roots by disrupting the "search and identify feeding site" behavior of the insect. All three types of effects are evaluated using the following protocols.

Adult and Nymphal Mortality Experiment

Approximately twenty four eggs of phylloxera were allowed to develop for up to] 30 days on standard excised grape roots. At around 30 days, some of the insects are nymphs while others are adults. New eggs were removed during the process. Insect infected roots were submerged into a test formula for 6 seconds then set aside to dry in the air. The percentage of live insects, as defined by growth, oviposition or limb movement, was determined after 5 days. An insect is considered dead if it abandons its feed site. In an initial test, doses of 20,000 ppm cinnamic aldehyde in water (i.e., 2% cinnamic aldehyde) with various additives were evaluated. Cinnamic aldehyde without any additives produced 83.3% mortality. With 1% Tween 80 added, 91.7% mortality was seen. With 6% $NaHCO_3$ added to a solution of 2% cinnamic aldehyde, 91.7% mortality was seen. With 1% Tween 80 and 6% $NaHCO_3$ added to a solution of 2% cinnamic aldehyde, 100% mortality was seen. Water with no additives produced no mortality, while a positive control solution of 250 ppm malathion in water gave 100% mortality.

Egg Hatch Experiment

Mixed age groups of 60 grape phylloxera eggs were established on filter paper (Whatman #1, 5.5 cm circles) in 50×9 mm sealing plastic petri dishes treated with 100 µl of solution. A selected concentration of a test formulation of 400 µl was added to the filter disk and the dish closed with the petri dish cover and placed in a plastic container box. After 6 hours, the box was placed in an environmental chamber at 24° C. in the dark. The eggs were placed in groups of 10. After one week, the percentage of hatch is determined. In an initial test, doses from 0.1 to 25,000 ppm cinnamic aldehyde in 6% $NaHCO_3$, 2% Tween 80 were evaluated with a single group of eggs at each dosage. Three replicates of the experiment were performed. The effects of the formulation were evaluated after 7 days and scored as the number of nymphs that died in the shell (DIS), or eggs that did not hatch completely (IH) (i.e., all died). LD50 and LD95 were determined by probit analysis. At 5000 ppm cinnamic aldehyde, all nymphs died in the shell. At 100 ppm, 88% died in the shell and the remaining 12% did not hatch completely. At 10 ppm, none died in the shell, but 100% of the eggs did not hatch completely. The addition of 0.86 ml of a 10° brix saponin solution in water to the formulation at 100 ppm increased the number of nymphs which died in the shell to 93%. Coniferyl aldehyde over the same dosage range (in 6% $NaHCO_3$, 2% Tween 80) was less potent. Although 10% of nymphs died in the shell at 5000 ppm, at 1000 ppm, 12% died in the shell and 85% hatched incompletely. All phylloxera eggs treated with $H_2O$ alone hatched; 100% of those treated with Carbofuran® (10 ppm) or malathion (250 ppm) died in the shell.

Example 5

Protocol for Aphid and White Fly

Activity of cinnamic aldehyde and/or coniferyl aldehyde against black bean aphid, *Tetranychus urticae*, and silverleaf white fly, *Bemisia argentifolii* is determined as follows:

Petri Dish Bioassay: Aphids

Petri dishes (60 mm) were treated with a particular formulation (e.g., 10–25,000 ppm) dissolved in water, and allowed to air dry. Twenty adult aphids (*Tetranychus urticae*) were put in each dish, (replicate 10 times). The mortality after three hours in contact with a treated plate was compared to that of aphids in petri dishes treated only with diluent. Malathion (250 ppm) was used as a positive control.

In initial experiments, cinnamic aldehyde at the indicated concentrations in 2% Tween 80 and 6% $NaHCO_3$ were tested. At concentrations of 2500 ppm and above, 100% of the aphids were killed. At 100 ppm and 10 ppm, 50% and 25% mortality was observed. Twenty-five percent mortality was observed with the concentration of 2% Tween 80 and 6% $NaHCO_3$ (no aldehyde added), and 100% of aphids were killed with malathion (250 ppm).

Plants are grown in 7.5 mm pot in potting soil in greenhouse. Cotton plants are used for white fly and sugar beets are used for aphids. When plants reach 3 leaf stage, they are infested with 60 of the specified anthropd (6 replications). The insect is allowed to settle and feed. The plant is sprayed to runoff (about 5 ml) with a formulation containing 100 to 200 pm, or 0.1 to 2 g/l concentration of a test formulation. The plant is covered with tall plastic cage (5 mm tall×10 mm diameter). The mortality of the insects after three days on the plants sprayed with a test formulation is determined and compared with that of insects on plants sprayed only with water.

Petri Dish Bioassay: Silver Leaf White Fly

Petri dishes (60 mm) were treated with a test formulation (e.g., 10–25000 ppm) dissolved in water, and allowed to air dry. Twenty adult silver leaf white fly were put in each dish, (replicate 10 times). The mortality after three hours in contact with a treated plate, was compared to that of silver leaf white fly in petri dishes treated only with diluent. Malathion at 250 ppm was used as a positive control.

TABLE 5

Effect of Cinnamic Aldehyde and Coniferyl Aldehyde Formulations on Aphid Mortality (Percent)

| | Aldehyde | | | |
| --- | --- | --- | --- | --- |
| Additive Formulation | None | Cinnamic Aldehyde (20 g) | Coniferyl Aldehyde (20 g) | Cinnamic Aldehyde (10 g) + Coniferyl Aldehyde (10 g) |
| | Percent Mortality | | | |
| None | 0 | | NT | NT |
| T80 (10 g) | | | NT | NT |
| $NaHCO_3$ | | | NT | NT |
| T80 + $NaHCO_3$ | 25 | 98.6 | NT | NT |
| Saponin (1% 10 brix) | NT | NT | NT | NT |
| Saponin + T80 | NT | NT | NT | NT |
| Saponin + $NaHCO_3$ | NT | NT | NT | NT |
| Malathion | 100 | NT | NT | NT |
| $H_2O$ (Neg. Control) | .07 | NT | NT | NT |

In initial experiments, cinnamic aldehyde at the indicated concentrations in 2% Tween 80 and 6% $NaHCO_3$ were tested. At concentrations of 2500 ppm and above, 100% of the silver leaf white fly were killed. At 100 ppm and 10 ppm, 50% and 25% mortality was observed. Twenty-five percent mortality was observed with the concentration of 2% Tween 80 and 6% NaHCO$_3$ (no aldehyde added), and 100% of silver leaf white fly were killed with malathion (250 ppm). See Table 6.

Example 6

Treatment of Nematodes

Various lands of nematodes infest plant tissue, including the stem and bulb nematode (*Ditylenchus dipsaci*) and rootknot nematode (*Meloidogyne spp.*). The treatment of stem nematode (*Ditylenchus dipsaci*) with various formulations containing cinnamic aldehyde is tested as follows:

Stem nematodes

Stem nematodes are extracted from garlic cloves by chopping the tissue into a mesh-bottomed beaker and suspending the mesh-bottomed beaker in a beaker of water. Nematodes migrate from the host tissue and sink down through the mesh into the bottom beaker. The supernatant water is removed and the nematodes remaining in the beaker are transferred to a watchglass and used in the treatment protocol as follows. Clear plastic trays are divided into open-topped cells measuring 20 mm×20 mm×20 mm. One half ml of tapwater at room temperature (19° C.) is pipetted into each cell. Ten nematodes are placed in each cell using an eyelash glued to a dissecting needle to handle each animal. One-half ml of one test solution is then added to each cell. Water is added to the control wells. Survival of nematodes in the cell is monitored by observation using a binocular microscope. The number of animals surviving 1, 5, 10, 20, 30 and 60 minutes after addition of the solutions is recorded. Mortality is assumed if individual nematodes are immobile and fail to respond to manipulation. The test is repeated three times.

TABLE 6

Effect of Cinnamic Aldehyde and Coniferyl Aldehyde Formulations on Silver Leaf White Fly Mortality (Percent)

| Additive Formulation | Aldehyde | | | |
|---|---|---|---|---|
| | None | Cinnamic Aldehyde (20 g) | Coniferyl Aldehyde (20 g) | Cinnamic Aldehyde (10 g) + Coniferyl Aldehyde (10 g) |
| | Percent Mortality | | | |
| None | 0 | 68.6 | NT | NT |
| T80 (10 g) | 14.5 | 72.1 | NT | NT |
| NaHCO$_3$ | 22.9 | 87.3 | NT | NT |
| T80 + NaHCO$_3$ | 25.0 | 100 | NT | NT |
| Saponin (1% 10 brix) | NT | NT | NT | NT |
| Saponin + T80 | NT | NT | NT | NT |
| Saponin + NaHCO$_3$ | NT | NT | NT | NT |
| Malathion (250 ppm) | 100 | NT | NT | NT |
| H$_2$O (Neg. Control) | 26.9 | NT | NT | NT |

In a double blind, concentrations of formula was tested for activity against root-knot nematode, *Meloidogyne javanica*. Nematodes were put in direct contact with the chemical and at 24 hour intervals, mortality was assessed both visually and by probing. *Meloidogyne javanica* were produced using hydroponics. The nematodes were harvested and used within 24 hours.

Approximately 100 nematodes in 0.07 mls of water were pipetted into a syracuse dish (Fisher) and 1 ml of test formulation was immediately pipetted into each dish. The dishes were then placed into plastic bags to retain moisture and prevent evaporation. Four syracuse dishes were used for each solution test formulation. Every 24 hours for 7 days, the solutions were examined and the first 10 nematodes encountered were assessed as either living or dead. This was based on morphological integrity of the nematode and touch. Moving nematodes were counted as living. As concentrations greater than 100 ppm cinnamic aldehyde in vehicle (2% Tween 80, 6% NaHCO$_3$), 100% nematodes were dead at 24 hours. At 10 ppm, 0%, 15%, 17.5% 22.5%, 27.5%, 52.5% and 52.5% were dead at 24, 48, 72, 96, 108, 132, and 156 hours respectively. There was no effect on mortality at 1 ppm and 0.1 ppm cinnamic aldehyde in vehicle. Addition of a 1:60 dilution 10 brix concentrate of *Yucca shidigera* saponin resulted in 100% mortality at 24 hours with the lowest concentration of cinnamic aldehyde in vehicle tested, 0.1 ppm. However, saponin alone had the same effect. EtOH (95%) killed all nematodes at 24 hours. Minimal effect of the vehicle on mortality was observed: 2.5% at 72 hours and 5% at 108 hours.

Example 7

Treatment of Strawberry Red Core (*Phytophtora Fragariae*)

Strawberry red core disease is caused by the fungus *Phytophtora fragariae* Hickman which is spread by means of infected planting material or soil infested with long-lived oospores of infected debris. Various formulations containing cinnamic aldehyde and/or coniferyl aldehyde are tested as follows: Macerated strawberry roots infected with *Phytophthora fragariae* are thoroughly mixed with infested compost and allowed to decompose for 4 to 6 weeks to produce a well rotted inoculum for treatment. This is divided into 1 kg lots and mixed with 1500 ml of a test formulation at different concentrations. After 10 minutes treatment, the compost is rinsed under running tap water on a 25 mm sieve for a minimum of 5 minutes to remove all traces of the test formulation. The compost is then put into 9-cm diameter plastic pots and planted with 4 strawberry plants per pot. Five pots are used for each treatment. Plants are grown in a controlled environment room at 15° C. and 18 h daylight; the compost is kept damp to encourage infection. Pots are placed on grids to avoid cross infection among treatments.

After 9 weeks the strawberry plant roots are washed free of compost and examined for signs of infection by cutting roots longitudinally and looking for red steles, and rotted or brown roots. All infections are confirmed by microscope examination of root pieces for the presence of oospores of *Phytophtora fragariae*.

Example 8

Stability of Cinnamic Aldehyde

Protocol to determine the stability of cinnamic aldehyde with and without an anti-oxidant over time.

Cinnamic aldehyde at 2% by weight added to a formula containing 2% Tween 80 and 6% sodium bicarbonate with and without the addition of vitamin E (tocopherol @ 1% of CNMA concentration).

The solutions to be maintained at 50° C. for two weeks. The solutions to be analyzed for cinnamic aldehyde concentration on regular intervals during the two week period by HPLC/UV and recorded (high pressure liquid chromatography ultra violet detection).

Example 9

Pitch Canker Disease

Pitch canker disease, caused by the fungus subglutinans f. sp. pini is characterized by a resinous exudation on the surface of shoots, branches, exposed roots and boles of infested trees. The host and geographic range of the pitch canker pathogen has greatly increased since it was first discovered in California in 1986. The pathogen has recently been discovered in Mexico and Japan. An association of Engraver beetles (Scolytidae: IPS species) as vectors of the Pitch Canker Fungus has been made by Fox, et al., (1991).

Bioassay undertaken in double blind with Professor Tom Gordon, University of California, Berkeley, using ProGuard PGXL formula and protocols. Bioassay based on inhibition of radial growth of *Fusarium subglutinans f sp. pini.*

Methods and Materials 1. 8 ml of product (concentration unknown) was pipetted into 200 ml of molten 2% potato dextros agar (PDA), the mixture was dispersed into five plastic petri dishes (25 ml dish).
2. Each of four plates was inoculated at the center with an agar plug transferred from a growing PDA culture of *Fusarium subglutinans f. sp. pini* (isolate SL-1, UCB). A fifth plate was left noninoculated as a control.
3. Steps 1 and 2 were repeated for each formulation of the unknown.
4. Four PDA plates amended with 5 ppm benomyl were inoculated as described in step 2.
5. Four unamended PDA plates were inoculated as described in step 2.
6. All inoculated and non-inoculated plates were incubated at 18° C. for five days, after which colony diameters were measured.

Results

Table 7 shows raw data averages for bioassay. Table 8 compares CNMA PGXL formula, CNMA PGXL formula+ saponin *Yucca schidegira* extract 10° BRIX) @ 0.86 ml, against controls.

TABLE 7

Radial Growth of *Fusarium Subglutinans* f, sp. *pini* (Data Averages)*

| Treatment | Colony diameter (cm) |
|---|---|
| PDA (unamended) | 4.038 |
| 10 ppm CNMA | 4.363 |
| 100 ppm CNMA | 4.238 |
| 100 ppm CNMA + Saponin | 4.300 |
| Glutaraldehyde 2% | 3.663 |
| 5,000 ppm CNMA + Saponin | 2.913 |
| 10 ppm CNMA + Saponin | 3.600 |
| $H_2O$ | 3.738 |
| 2,500 ppm CNMA | 3.513 |
| 2,500 ppm CNMA + Saponin | 3.600 |
| Saponin | 4.138 |
| 5,000 CNMA | 2.908 |
| Formula Blank | 4.380 |
| 12,500 CNMA + Saponin | 0.000 |
| 25,000 CNMA | 0.000 |
| 5 ppm Benomyl (Positive Control) | 0.000 |
| 12,500 ppm CNMA | 0.000 |
| 25,000 CNMA + Saponin | 0.000 |

TABLE 8

Radial Growth of *F. Subglutinans* f. sp. *pini*

| | Treatments | |
|---|---|---|
| ppm | PGXL CNMA colony diameter (cm) | PGXL CNMA + Saponin (.86 ml) colony diameter (cm) |
| 10 | 4.36 | 4.09 |
| 100 | 4.24 | 4.3 |
| 2,500 | 3.51 | 3.6 |
| 5,000 | 2.98 | 2.91 |
| 12,500 | 0 | 0 |
| 25,000 | 0 | 0 |
| Controls | colony diameter (cm) | |
| 2% Glutaraldehyde | 3.66 | |
| $H_2O$ | 3.74 | |
| 5 ppm Benomyl | 0 | |
| PDA (unamended) | 4.04 | |

Example 10

Overproduction of Aromatic Aldehydes in Transgenic Plants

20 μg of polyA RNA is prepared and cDNA synthesized. Part of this is cloned into lambda-ZAP II vector (a commercially available cloning vector). At least 500,000 recombinants are screened using an oligonucleotide probe designed from conserved sequences of cloned CA4H and CAD genes obtained from GenBank, or designed from peptide sequence of purified protein from the intended host plant. Strongly hybridizing clones are selected and used to rescreen the cDNA library. The resulting clones are sequenced to enable the introduction of appropriate gene sequences into a plant expression cassette in either antisense or sense orientation. The antisense and sense constructs are introduced into *Agrobacterium tumefaciens* LBA4404 by direct transformation following published procedures. Tobacco (*N. tabacum*, variety Samsun) leaf discs are transformed using well established published procedures (Horsch, et al., (1985 *Science* 227:1229–1231. Plants containing either CA4H or CAD constructs are identified by PCR and selected for further analysis.

Plant material from both transformed and untransformed control plants is used for determinations of CA4H and CAD enzyme activity using well established published assays. Plants in which the activity of CA4H or CAD has been reduced to less hand 20% of that seen in control plants are selected for further analysis. Selected plants with low CA4H activity are crossed with plants with low CAD activity and progeny inheriting both gene construct are selected by PCR. Plants with suppressed CA4H and suppressed CAD activity are analyzed for flavonoid aldehyde production using standard published procedures.

Example 11

Production of Aromatic Aldehydes in Microbial Systems

A cDNA library is generated using RNA extracted from six week old tobacco stems. 20 μg of polyA RNA is prepared and cDNA synthesized. Part of this is cloned into lambda-ZAP II vector (a commercially available cloning vector). At least 500,000 recombinants are screened using an oligonucleotide probe designed from peptide sequence sequences of CCoAr protein purified from six week old tobacco stem tissue using the protocol of Goffner, et al., *Plant Physiol.* (1994) 106:625. Strongly hybridizing clones are selected and used to rescreen the cDNA library. The resulting clones are sequenced to enable the identification of full-length cDNA inserts and the introduction of appropriate CCoAR gene sequences into yeast expression vector pMTL8110 (Faulkner, et al (1994) *Gene* 143:13–20. The coding sequences for *Rhodosporidium torulides* phenylalanine ammonia lyase (PAL; GenBank locus RHDPAL) and a parsley 4-coumarate:CoAl ligase (4CL; GenBank locus PC4CL1AA) are similarly introduced into equivalent yeast expression vectors. The PAL,4CL and CCoAR constructs are used to transform *Saccharomyces cerevisiae* strains by electroporation using established published procedures (Becker, and Guarente, *Methods in Enzymology* 194:182–187, 1991; Simon, (1993) *Methods in Enzymol* 217:478–483. Transformants are selected on minimal medium lacking leucine. Transformant strains carrying all three gene constructs are identified by PCR and selecter for further analysis.

Extracts from both transformed and untransformed control strains are used for determinations of PAL, 4CL and CCoAR enzyme activities using well established published assays. Strains in which the activity of PAL, 4CL and CCoAR is significantly greater than the background activity detected in control strains are selected for further analysis. Selected strains are analyzed for aromatic aldehyde production using standard published procedures and those producing significant amounts of cinnamaldehyde are selected for optimization of fermentation conditions.

As the above results show, potted roses or field grown roses sprayed to run off with an emulsion containing cinnamic aldehyde and sodium bicarbonate and concomitantly sprayed with saponin remained free of powdery mildew and rust for up to 56 days as compared to plants sprayed only with water. The plants also remained free of aphids. It has been reported that induced systemic resistance to powdery mildew of roses sprayed with Rubigon averages about 20 days. Mean disease control determinations of approximately 70% were obtained for roses sprayed with an aqueous solution of cinnamic aldehyde and coniferyl aldehyde or emulsions containing sodium bicarbonate and cinnamic aldehyde and/or coniferyl aldehyde. In parallel experiments, Benomyl gave a mean disease control of approximately 80%.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for protecting a chrysanthemum from infestation and attack by powdery mildew, said method comprising:

contacting one or more parts of said chrysanthemum with a formulation comprising an amount of from 2.5 to 50 g/l of cinnamic aldehyde, wherein aid amount is sufficient to provide at least 70% inhibition of the growth of aid powdery mildew, wherein said formulation has a phytoxicity rating of 1 or less for said chrysanthemum, and wherein said formulation does not include an anti-oxidant whereby said chrysanthemum is protected from infestation and attack by said powdery mildew.

2. A method for protecting a bell pepper, a lettuce or a tomato plant from infestation and attack by powdery mildew, said method comprising:

contacting one or more parts of said plant with a formulation comprising amount of from 2.5 to 50 g/l of cinnamic aldehyde, wherein said amount is sufficient to provide at least 70% inhibition of the growth of said powdery mildew, wherein said formulation has a phytotoxicity rating of 1 or less for said plant, and wherein said formulation does not include an anti-oxidant, whereby said plant is protected from infestation and attack by said powdery mildew.

3. A method for protecting a cantaloupe or a grape plant from infestation and attack by powdery mildew said method comprising:

contacting one or more parts of said plant with a formulation comprising amount of from 2.5 to 50 g/l of cinnamic aldehyde, wherein said amount is sufficient to provide at least 70% inhibition of the growth of said powdery mildew, wherein said formulation hag a phytotoxicity rating of 1 or less for said plant, and wherein aid formulation does not include an anti-oxidant whereby said plant is protected from infestation and attack by said powdery mildew.

4. A method for protecting a citrus tree from infestation and attack by powdery mildew, said method comprising:

contacting one or more parts of said citrus tree with a formulation comprising an amount of from 2.5 to 50 g/l of cinnamic aldehydes, wherein said anoint is sufficiently to providing at least 70% inhibition of the growth of said powdery mildew, wherein said formulation has a phytoxicity rating of 1 or legs for said rose, and wherein said formulation does not include an anti-oxidant, whereby said citrus tree is protected from infestation and attack by said powdery mildew.

5. A method for protecting a rose from infestation and attack by powdery mildew, said method:

contacting one or more parts of said rose with a formulation comprising an amount of from 2.5 to 50 g/l of cinnamic aldehyde, wherein said anoint is sufficient to provide at least 70% inhibition of the growth of ,aid powdery mildew, wherein said formulation has a phytoxicity rating of 1 or less for said rose, and wherein said formulation does not include an anti-oxidant, whereby said rose is protected from infestation and attack by said powdery mildew.

6. A method for protecting a cabbage plant from infestation and attack by powdery mildew, said method comprising:

contacting one or more parts of said cabbage plant with a formulation comprising an amount of from 2.5 to 90 g/l of cinnamic aldehyde, wherein said amount is sufficient to provide at least 70% inhibition of the growth of said powdery mildew, wherein said formulation has a phytoxicity rating of 1 or less for said cabbage plant, and wherein said formulation does not include an anti-oxidant, whereby said cabbage plant is protected from infestation and attack by said powdery mildew.

7. A method for protecting a bent grass or a turf grass plant from infestation and attack by powdery mildew, said method comprising:

contacting one or more parts of ,aid plant with a formulation comprising an amount of from 2.5 to 50 g/l of cinnamic aldehyde, wherein said amount is sufficient to provide at least 70% inhibition of the growth of said powdery mildew, wherein aid formulation has a phytotoxicity rating of 1 or less for said plant and wherein said formulation does not include an anti-oxidant whereby said plant is protected from infestation and attack by aid powdery mildew.

8. A method for protecting a grass from infestation and attack by *Sclerotinia homoeocarca*, said method comprising:

contacting one or more parts of said grass with a formulation comprising an amount of from 2.5 to 50 g/l of cinnamic aldehyde, wherein said amount is sufficient to provide at least 70% inhibition of the growth of *Sclerotinia homoeocarca*, wherein said formulation has a phytotoxicity rating of 1 or less for said grass, and wherein said formulation does not include an anti-oxidant, whereby said grass is protected from infestation and attack by said *Sclerotinia homoeocarca*.

9. A method for protecting a rose from infestation and attack by at least one pathological organism, said method comprising:

contacting one or more parts of said rose with a formulation comprising an amount of from 2.5 to 50 g/l of coniferyl aldehyde, wherein said amount is sufficient to provide at least 70% inhibition of the growth of at least one pathological organism selected from the group consisting of powdery mildew and rust, wherein said formulation has a phytotoxicity rating of 1 or less for said rose, and wherein said formulation does not include an anti-oxidant, whereby said rose is protected from infestation and attack by said at least one pathological organism.

10. A method for protecting a rose from infestation and attack by powdery mildew, said method comprising:

contacting one or more parts of said rose with a formulation comprising an amount of from 2.5 to 50 g/l of cinnamic aldehyde and from 2.5 to 50 g/l of coniferyl aldehyde, wherein said amount is sufficient to provide at least 70% inhibition of the growth of said powdery mildew, wherein said formulation has a phytotoxicity rating of I or less for said rose, and wherein said formulation does not include an additional anti-oxidant, whereby said rose is protected from infestation and attack by said powdery mildew.

11. A method for protecting a rose from infestation and attack by one or more pathological organism, said method comprising:

contacting one or more parts of said rose with a formulation comprising an amount of from 2.5 to 50 g/l of cinnamic aldehyde, wherein said amount is sufficient to provide at least 70% inhibition of the growth of a pathological organism selected from the group consisting of powdery mildew and rust, wherein said formulation has a phytotoxicity rating of I or less for said rose, and wherein said formulation does not include an anti-oxidant, whereby said rose is protected from infestation and attack by said one or more pathological organism.

12. A method for protecting a grape from infestation and attack by powdery mildew, said method comprising:

contacting one or more parts of said grape with a formulation comprising an amount of from 2.5 to 50 g/l of cinnamic aldehyde, wherein said amount is sufficient to provide at least 70% inhibition of the growth of aid powdery mildew, wherein said formulation has a phytotoxicity rating of 1 or less for said grape, and wherein said formulation does not include an anti-oxidant, whereby said grape is protected from infestation and attack by said powdery mildew.

13. The method according to any one of claims 1, 2, 3, 4, 5, 6, 7, 8, 9, 10, 11 or 12, wherein said formulation further comprises saponin.

14. The method according to any one of claims 1, 2, 3, 4, 5, 6, 7, 8, 9, 10, 11 or 12, wherein said contacting is by spraying.

15. The method according to any one of claims 1, 2, 3, 4, 5, 6, 7, 8, 9, 10, 11 or 12, wherein said formulation is an aqueous formulation.

16. The method according to any one of claims 1, 2, 3, 4, 5, 6, 7, 8, 9, 10, 11 or 12, wherein said one or more parts of said plant are leaves.

\* \* \* \* \*